US009867685B2

(12) United States Patent
Roll et al.

(10) Patent No.: US 9,867,685 B2
(45) Date of Patent: *Jan. 16, 2018

(54) MINIMALLY INVASIVE IMPLANT AND METHOD

(71) Applicant: Boston Scientific Scimed, Inc., Marlborough, MA (US)

(72) Inventors: Jessica L. Roll, Maple Grove, MN (US); John Fritz Otte, St. Anthony, MN (US); Mona N. Dahdah, West St. Paul, MN (US); Brian G. Fischer, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,525

(22) Filed: Apr. 27, 2015

(65) Prior Publication Data

US 2015/0238297 A1 Aug. 27, 2015

Related U.S. Application Data

(63) Continuation of application No. 13/335,472, filed on Dec. 22, 2011, now Pat. No. 9,017,243, which is a continuation-in-part of application No. 13/060,467, filed as application No. PCT/US2009/054909 on Aug. 25, 2009, now Pat. No. 8,968,181.

(60) Provisional application No. 61/426,117, filed on Dec. 22, 2010, provisional application No. 61/091,586, filed on Aug. 25, 2008.

(51) Int. Cl.
*A61F 2/00* (2006.01)
*A61B 17/04* (2006.01)
*A61B 17/06* (2006.01)
*A61B 17/00* (2006.01)

(52) U.S. Cl.
CPC ........ *A61F 2/0045* (2013.01); *A61B 17/0401* (2013.01); *A61B 17/06109* (2013.01); *A61B 2017/00805* (2013.01); *A61B 2017/0409* (2013.01); *A61B 2017/0412* (2013.01); *A61B 2017/0414* (2013.01); *A61B 2017/0417* (2013.01); *A61B 2017/0464* (2013.01); *A61F 2220/0016* (2013.01); *A61F 2250/0097* (2013.01)

(58) Field of Classification Search
CPC .... A61F 2/0004; A61F 2/0031; A61F 2/0036; A61F 2/0045; A61F 2/0063
USPC .......................... 600/29–32, 37; 128/DIG. 25
See application file for complete search history.

(56) References Cited

U.S. PATENT DOCUMENTS

| 6,221,005 | B1 * | 4/2001 | Bruckner | A61B 17/064 128/DIG. 25 |
| 6,641,525 | B2 * | 11/2003 | Rocheleau | A61B 17/0401 600/30 |
| 9,017,243 | B2 * | 4/2015 | Roll | A61B 17/0401 600/37 |

(Continued)

*Primary Examiner* — John Lacyk
(74) *Attorney, Agent, or Firm* — Brake Hughes Bellermann LLP

(57) ABSTRACT

Apparatus and methods are provided for treating urinary incontinence, fecal incontinence, and other pelvic defects or dysfunctions, in both males and females, using one or more lateral implants to reinforce the supportive tissue of the urethra. The implants can be configured as a sling device having at least one extension arm and a tissue support portion having an eyelet, wherein a portion of the at least one extension arm is adapted to slide through and adjustably attach with the eyelet.

13 Claims, 17 Drawing Sheets

(56) References Cited

U.S. PATENT DOCUMENTS

2011/0112357 A1\* 5/2011 Chapman ........... A61B 17/0401
600/37

\* cited by examiner

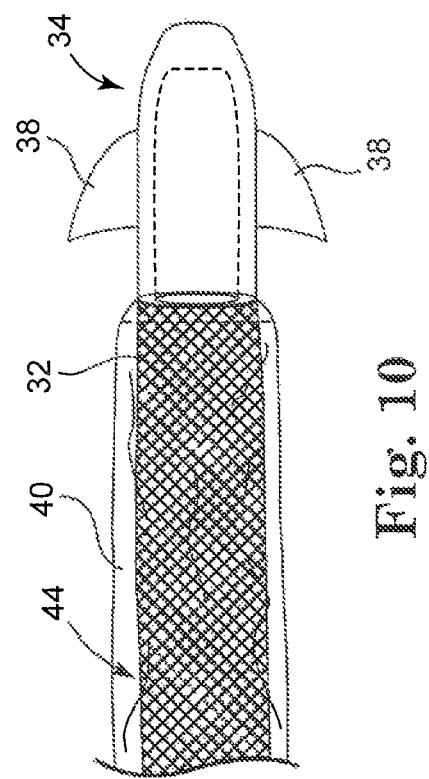
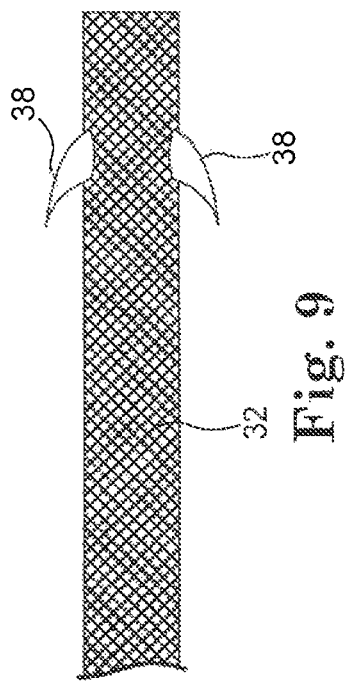
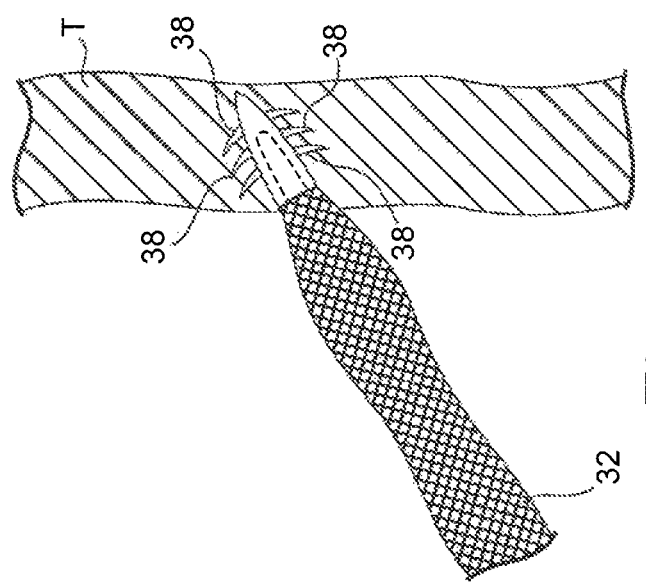

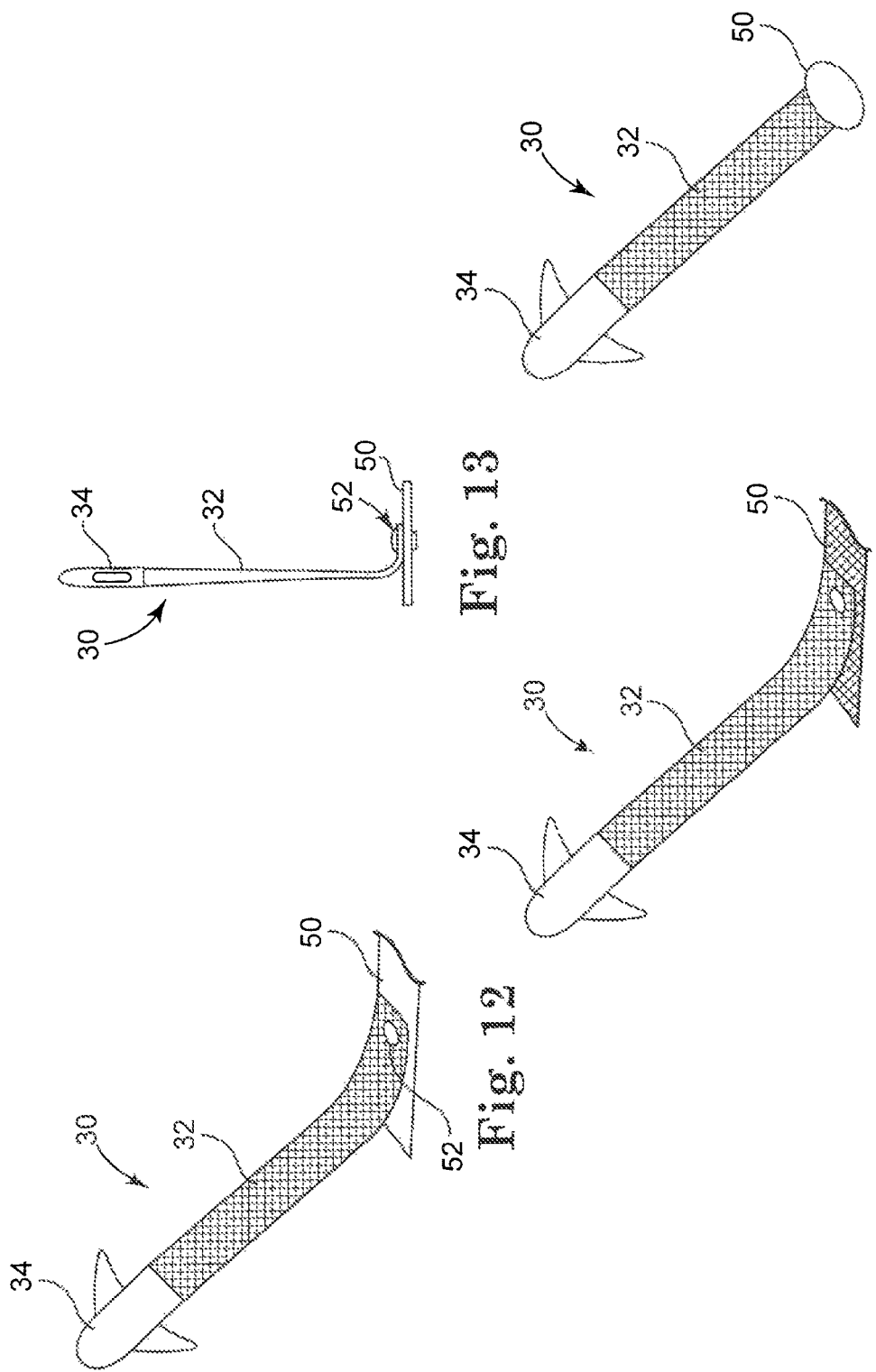

MINIMALLY INVASIVE IMPLANT AND METHOD

RELATED APPLICATION

This application is a Continuation of U.S. application Ser. No. 13/335,472, filed Dec. 22, 2011, which is a Continuation-In-Part of U.S. application Ser. No. 13/060,467, filed May 4, 2011, and now issued as U.S. Pat. No. 8,968,181, and which claims priority to and the benefit of U.S. Provisional Application No. 61/426,117, filed Dec. 22, 2010, and U.S. application Ser. No. 13/060,467 claims priority to and the benefit of International PCT Patent Application No. PCT/US2009/054909, filed Aug. 25, 2009, which claims priority to and the benefit of U.S. Provisional Application No. 61/091,586, filed Aug. 25, 2008; with each of the above-referenced applications being fully incorporated herein by reference in their entirety.

FIELD OF THE INVENTION

The present invention relates to apparatus, tools and methods for treating pelvic conditions by providing and using one or more pelvic implants to support pelvic tissue.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. FIG. 1 schematically illustrates the relevant female anatomy. The urethra 16 is the tube that passes urine from the bladder 14 out of the body. The narrow, internal opening of the urethra 16 within the bladder 14 is the bladder neck 18. In this region, the bladder's bundled muscular fibers transition into a sphincteric striated muscle called the internal sphincter. FIG. 2 schematically illustrates the relevant male anatomy. The urethra 16 extends from the bladder neck 18 to the end of the penis 22. The male urethra 16 is composed of three portions: the prostatic, bulbar and pendulus portions. The prostatic portion is the widest part of the tube, which passes through the prostate gland 24. FIG. 3 is a schematic view of the anatomy of the anus and rectum. The rectum 1 is the most distal portion of the gastrointestinal tract. The exterior opening of the rectum is the anus 2. Fecal continence is related to control of the exterior sphincter 3 and interior sphincter 4 of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder" "frequency/urgency syndrome" or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. With regard to surgical treatments, the purported "gold standard" is the Burch Colposuspension, in which the bladder neck is suspended. Mid-urethral slings have been similarly effective. One type of procedure, found to be an especially successful treatment option for SUI in both men and women, is a sling and support procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension structures or sutures to a point of attachment (e.g., tissue or bone) through an abdominal and/or vaginal incision.

Although serious complications associated with sling procedures are infrequent, they can occur. Complications for certain sling procedures may include urethral obstruction, development of de novo urge incontinence, hemorrhage, prolonged urinary retention, infection, damage to surrounding tissue and erosion.

Fecal incontinence, like urinary incontinence, has proven to be challenging to treat. Patients whose fecal incontinence is caused by external anal sphincter injury is treated surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic graciloplasty, artificial sphincter procedures, and sacral nerve stimulation. Success has been limited, and the various treatment modalities can result in morbidity.

There is a desire for a minimally invasive yet highly effective treatment modality that can be used with minimal to no side effects for the treatment of both urinary and fecal incontinence. Further, the method of treatment should also improve the quality of life for patients.

SUMMARY OF THE INVENTION

The present invention can include surgical instruments, implantable articles, and methods for urological applications, particularly for the treatment of stress and/or urge urinary incontinence, fecal incontinence, and prolapse and perineal floor repairs. As noted, the usual treatments for SUI include placing a sling to either compress the urethral sphincter or to elevate or support the neck of the bladder defects.

Embodiments of the present invention can include apparatus and methods for treating urinary incontinence, fecal incontinence, and other pelvic defects or dysfunctions, in both males and females using one or more lateral implants to reinforce the supportive tissue of the urethra. The implants are configured to engage and pull (e.g., pull up) lateral urethral support (e.g., endopelvic fascia) tissue to cause the sub-urethral tissue to tighten and provide slack reduction for improved support. As such, the implants of such embodiments can be utilized to eliminate the need for mesh or other supportive structures under the urethra that is common with other incontinence slings. The implants can be shaped to facilitate such support, e.g., provided with anchoring end portions or configurable in "U," "V" or like shapes. Further, one or more anchors or tissue engagement portions can be employed to attach and stabilize the implants to the tissue. Other embodiments of the present invention can include a supportive sling implant having one or more arm portions and a tensioning rod. Such embodiments can be provided in a traditional supportive configuration under the urethra, or laterally positioning with respect to the urethra, as described herein. In various such embodiments, the sling can include a tissue support portion having a first eyelet and a second eyelet, a first extension arm, and a second extension arm. The first extension arm can include an anchor portion and an opposing end adjustment element, with at least a length of the first extension arm adapted to slide through the first eyelet of the tissue support portion. Similarly, the second extension arm can include an anchor portion and an opposing end adjustment element, with at least a length of the first extension arm adapted to slide through the second eyelet of the tissue support portion.

The support portion can be included with one of the extension arms to provide a two-piece construct. For instance, the first extension arm and its corresponding support portion can include the eyelet and an anchoring portion. The second arm extension can slidably engage with the eyelet to define the elongate sling. Alternatively, the support portion can be a separate element of a three-piece construct. As such, the support portion for such embodiments can include two or more eyelets. Two separate extension arms can be included with such embodiments (e.g., each with anchors and adjustment elements), with each extension arm adapted to slidably engage with a respective eyelet of the separate support portion.

Certain embodiments of the implant or sling can include one or more indicia to assist in deployment, adjustment and tensioning of the implant or sling.

Embodiments of the present invention can provide smaller implants, fewer implant components, thus reducing the size and number of incisions, improving implant manipulation and adjustment, and the complexity of the insertion and deployment steps.

BRIEF DESCRIPTION OF THE DRAWINGS

FIG. 9 shows a pelvic implant device having anchoring members along a portion of the extension portion in accordance with embodiments of the present invention.

FIG. 10 shows an anchoring pelvic implant device in accordance with embodiments of the present invention.

FIG. 11 shows a pelvic implant device having a multi-barbed anchor in accordance with embodiments of the present invention.

FIGS. 12-15 show various pelvic implant devices with a leading anchor and a trailing base or bulk anchor in accordance with embodiments of the present invention.

DETAILED DESCRIPTION OF PREFERRED EMBODIMENTS

Figure 1:
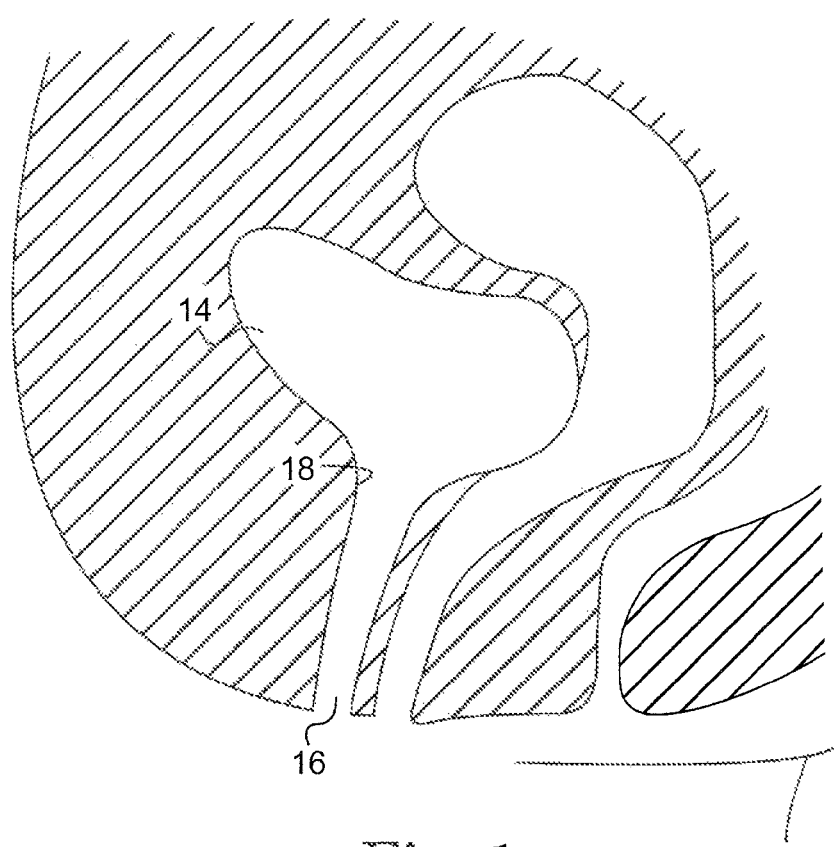
FIG. 1 shows a schematic view of the female urinary system.
Figure 2:
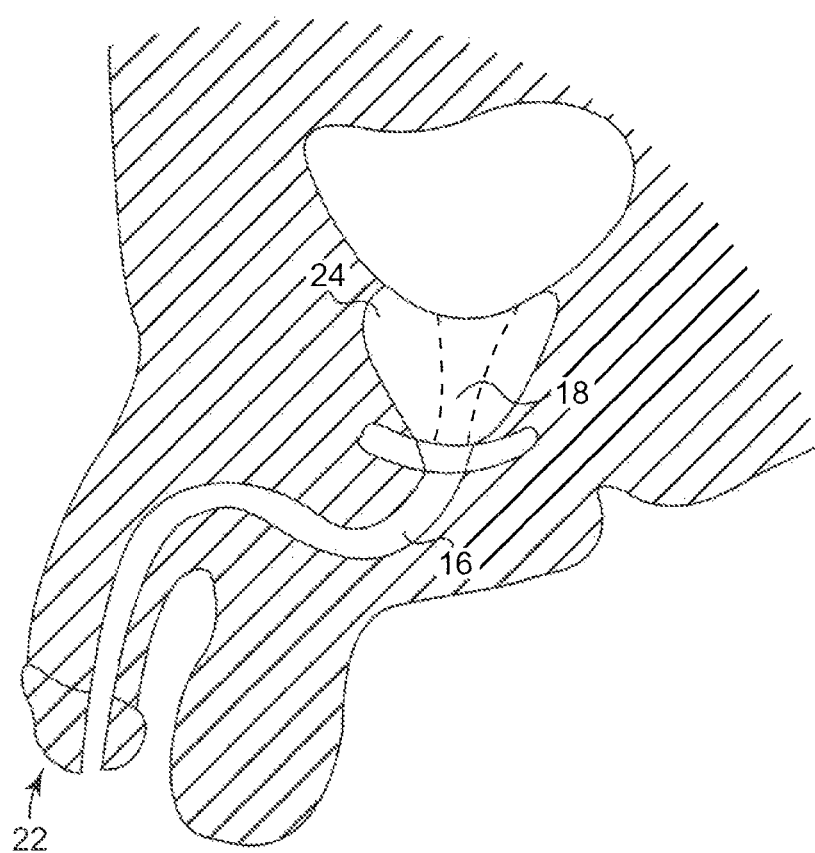
FIG. 2 shows a schematic view of the male urinary system.
Figure 3:
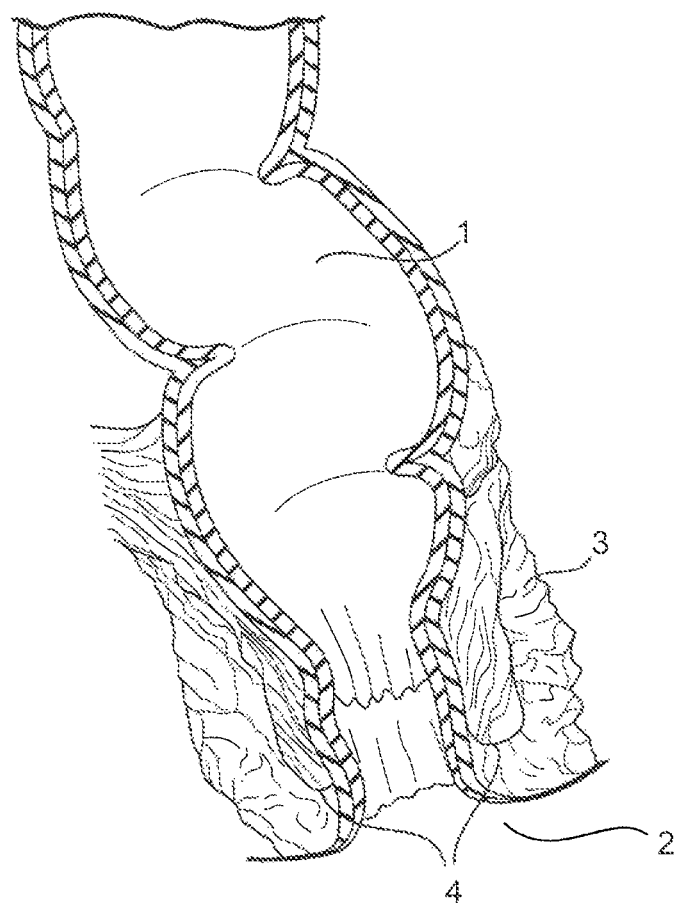
FIG. 3 shows a schematic view of the anatomy of the anus and rectum.

Referring generally to FIGS. 1-41, like reference numerals can designate identical, similar or corresponding parts throughout the views. The following description is meant to be illustrative only, and not limiting other embodiments of this invention that will be apparent to those of ordinary skill in the art in view of this description.

One aspect of the present invention is an apparatus and method of treating urinary incontinence in males or females. In various embodiments, one or more implants or implant members are placed in strategically located positions to pull up or otherwise tighten tissue and/or muscle lateral to the urethra to generally re-establish the original anatomical structure of the patient. Various systems, devices, structures, techniques and methods, alone or in combination, as disclosed in U.S. Pat. Nos. 6,911,003, 6,612,977, 6,802,807, 2002/0161382, 2004/0039453 and 2008/0045782, and International PCT Publication No. 2008/057261, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

Figure 4:
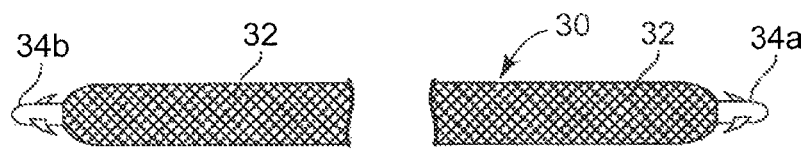
FIG. 4 shows a pelvic implant device in accordance with embodiments of the present invention.
Figure 5:
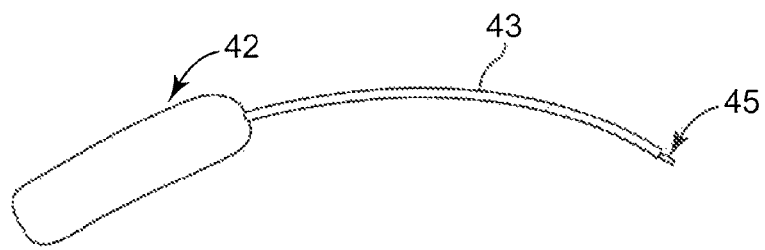
FIG. 5 shows an introducer or insertion device capable of use with embodiments of the present invention.

Various embodiments of the present invention can include a tensioning or support implant device 30 having an extension portion 32 and one or more engagement portions 34, as shown in FIG. 4. The one or more engagement portions can include a first anchor 34a at a first or leading end of the tensioning device 30, with a second anchor 34b provided at an opposite trailing end of the device 30. The extension portion 32 can be constructed of a compatible mesh or like porous material known for use and compatibility with urethral slings, other pelvic support devices, and the like. The mesh material can facilitate the infiltration of tissue and cells within the extension portion 32 to promote tissue in-growth and, in turn, fixation of the device 30 to the surrounding anatomical structure. The extension portion 32 can also include protrusions, serrated edges, extending fibers, or similar structural features to promote tissue fixation and in-growth. In other embodiments, the extension portion 32 can be constructed of a flexible, or semi-rigid, length of a compatible generally non-porous material. The length and flexibility of the device 30 and corresponding extension portion 32 can vary greatly depending on the particular procedure and anatomical support application. The extension portion 32 can be generally planar at introduction, pre-shaped or pre-formed, or otherwise configured to allow for adaptation, manipulation and shaping during the implantation procedure. Various embodiments of the extension portion 32 can be capable of forming into a generally V-shaped or U-shaped device (FIG. 6), or otherwise adapted for flexible or selective manipulation and traversal through, around and/or along various tissue and muscles of the pelvic region. In certain embodiments, the length of the device 30 can range from 0.5 to 6 cm. It is also possible to have lengths greater than or less than 0.5 to 6 cm.

In certain embodiments, the implant can be constructed in the form of a collapsible synthetic mesh patch, and can include an adhesive covering (e.g., fibron glue). Further, an umbrella-like feature can be included with wire splines or members extending from the patch. The umbrella-like feature can be connected with the patch via a connection structure, such as a ring, fastener, etc. A portion of the implant introducer (e.g., plunger and/or wire) can be configured to advance the patch and deploy and/or expand the umbrella-like feature to provide tissue engagement for the patch.

Figure 6:
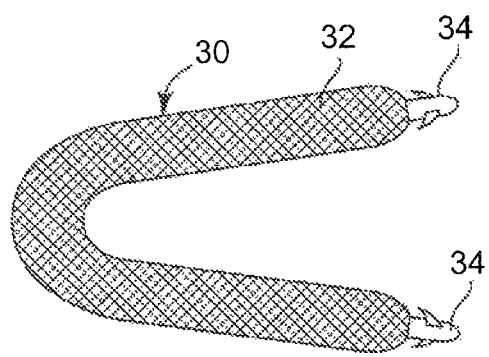
FIG. 6 shows a generally U-shaped pelvic implant device in accordance with embodiments of the present invention.
Figure 7:
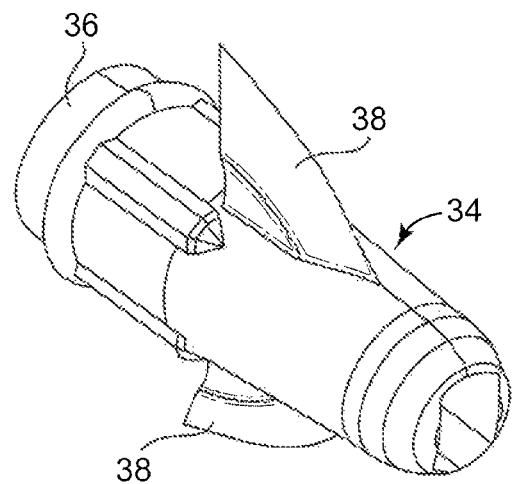
FIG. 7 shows an anchor of a pelvic implant device in accordance with embodiments of the present invention.
Figure 8:
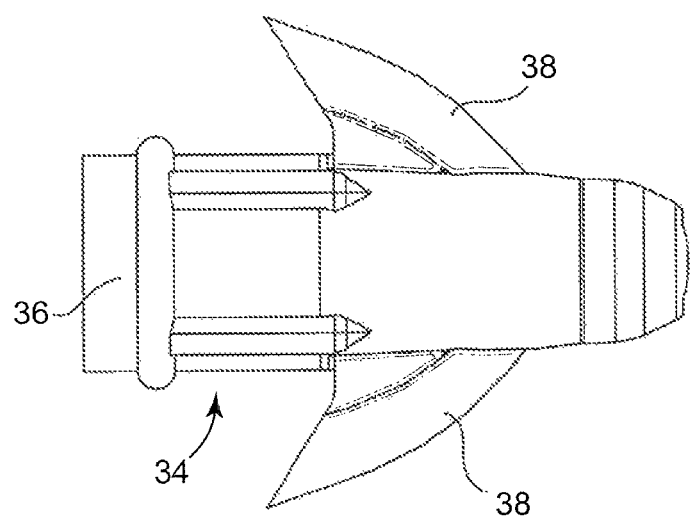
FIG. 8 shows a side view of the pelvic implant device anchor of FIG. 7.

The one or more engagement portions 34 can be configured as fixating, or self-fixating, tips or anchors 34 adapted for penetration and fixation within target tissue or muscle (T) of the pelvic region. As shown in FIGS. 4, 6 and 7-11, the anchors 34 can vary in shape, size and placement along the device 30. For instance, as shown in FIGS. 4 and 6, the anchors 34 can be integrated, attached or otherwise provided proximate the ends of the extension portion 32. The extension portion 32 can be connected to the anchors 34 via an end portion 36 of the anchors 34. A myriad of attachment structures or techniques can be utilized to connect the ends of the extension portion 32 to the end portion 36 of the anchors 34. Further, the anchors 34 can include opposing tines or barbs 38 to facilitate penetration and fixation within the target tissue. Other embodiments, such as those depicted in FIGS. 9-11, can include one or more tines 38 provided along portions of the extension portion 32 (FIG. 9), or a plurality of barbs 38 disposed along the anchors 34 (FIG. 11). Moreover, the one or more engagement portions 34 can be configured as toggle bolt anchors (FIG. 26), tubular members, planar members, bulbous members and the like, any of which can be constructed of compatible polymers, metals, mesh or non-porous materials, or bio-absorbable or non-absorbable materials. As depicted and described herein, the engagement portions 34 can be adapted to engage various target tissue regions, including the endopelvic fascia, the rectus fascia/muscle, the obturator muscle, and other anatomical structures of the pelvis.

In addition, a sheath or sleeve 40 can be selectively provided along a length of the extension portion 32 to facilitate introduction and insertion of the device 30 within the pelvic region of the patient, as depicted in FIG. 10. One or more insertion or introduction devices 42 can be employed to facilitate traversal of the device 30 within the pelvic region, and to facilitate deployment of the device 30 (e.g., anchors 34) into the target tissue location. Various known insertion devices 42 can be utilized, including those disclosed in the previously-incorporated patent references. A needle embodiment of the device 42 can include a handle, a tubular member 43 (straight or curved), and a tip 45 adapted for selective engagement with one or more components of the implants disclosed herein. As depicted in FIG. 10, the extension portion 32 can include a plurality of fibrous material or strands 44 adapted to further promote tissue in-growth and fixation.

As detailed herein, various embodiments of the present invention are configured to treat urinary incontinence by providing support to the tissue or anatomical structure proximate or surrounding the urethra, rather than providing more conventional hammock-like support under the urethra. The device 30 and engagement aspects of the invention for such embodiments can vary greatly, as detailed herein.

As shown in FIGS. 12-15, the device 30 can include the barbed anchor 34 at a leading end of the extension portion 32 and a bulk base member 50 at the opposite trailing end. The extension portion 32 can be constructed of a mesh material (FIG. 12), or another porous or non-porous material (FIGS. 14-15). Further, the base member 50 can be mesh, or another porous or non-porous material, and can take on any variety of shapes, including planar, bulbous, tubular, etc. The base member 50 can be integrated with the extension portion 32, attached using fasteners 52 (e.g., rivet), bonded, or otherwise attached utilizing known structures and techniques. In other embodiments, the extension portion 32 can be made of random fibers, or a weaved, braided, twisted, or knitted polymer material.

Figure 16:
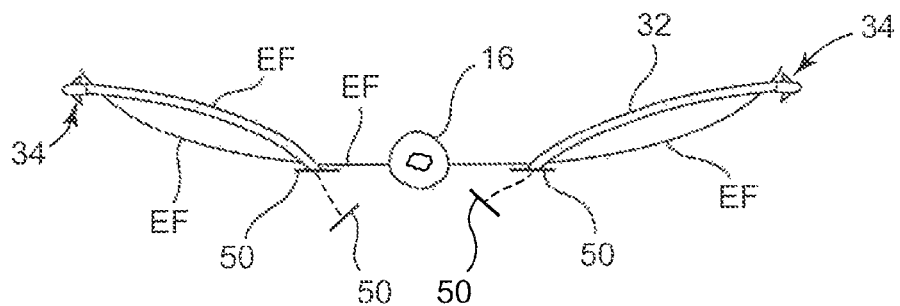
FIG. 16 shows the implantation of pelvic implant devices in the lateral urethral support tissue in accordance with embodiments of the present invention.

As depicted in FIG. 16, the device 30 can be inserted along a path generally toward the obturator foramen for penetration through the endopelvic fascia (EF) on either or both sides of the urethra 16. As such, the anchors 34 are positioned for fixation with tissue or muscle proximate the fascia so that the base member 50 is disposed on the entry side of the fascia. The base member 50 of each device 30 can be sized and shaped such that it remains on the entry side of the fascia and can include one or more anchors, protrusions or similar structures to provide additional engagement and retention against the fascia. The anchors 34 are advanced and positioned to penetrate through or otherwise engage with selective target tissue such that the laterally extending sub-urethral tissue, such as the endopelvic fascia, is pulled upward to remove slack and relocate the fascia and/or urethra to a more optimal and correct anatomical position. Other adjustment mechanisms and techniques can also be used to raise the fascia to provide the desired tightening or slack reduction in the laterally extending urethral support tissue. The devices 30 of FIGS. 14-15 function in the same manner, except that the extension portion 32 and base members 50 can assume different design configurations and can be constructed of different materials, such as relatively stiff or flexible polymers, mesh, non-porous mesh and other known compatible materials.

Structures or portions of the various embodiments detailed herein can be constructed of materials such as polypropylene, polyglycolide, poly-l-lactides, or other known biodegradable (re-absorbable) or non-biodegradable polymers. Further, growth factors or stem cells can be seeded or otherwise provided with one or more of the components of the device 30 to facilitate healing or tissue in-growth. In addition to introduction and deployment of the device 30 with a needle introducer device, a cannula or catheter system can be utilized as well.

Figure 17:
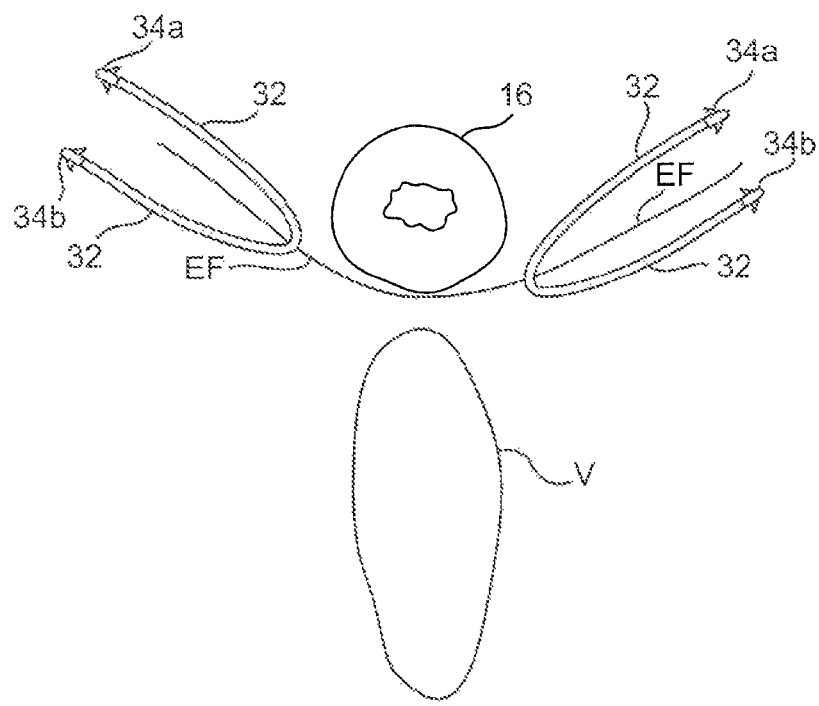
FIG. 17 schematically shows the implantation of U-shaped pelvic implant devices in the lateral urethral support tissue in accordance with embodiments of the present invention.

The embodiment of FIGS. 16-17 includes an implant device 30 having the extension portion 32 and one or more engagement or anchor portions 34 provided at an end region of the extension portion 32. The device 30 can be designed with a level of flexibility allowing a user to easily direct and advance the device 30 and to allow for manipulation of the device 30 into a generally U-shaped or similar configuration during deployment and anchoring. In one embodiment, the device 30 is adapted to generally augment the lateral tissue of the supportive pelvic floor of the patient. For instance, a first of the anchors 34a can be inserted through the endopelvic fascia for fixation within tissue. As such, the other anchor 34b can be adjusted or pulled to tighten and raise the supportive urethral tissue. One or more of the anchors 34a, 34b can be fixated to tissue near or at the obturator internus muscle or obturator membrane. Upon pulling the support tissue up to generally obtain the correct anatomical urethral support, the second anchor is fixated within the proximate tissue, with the bend of the extension portion 32 extending through the fascia. This process can be repeated for the supportive tissue on the other side of the urethra to provide bilateral augmentation and support.

Figure 18:
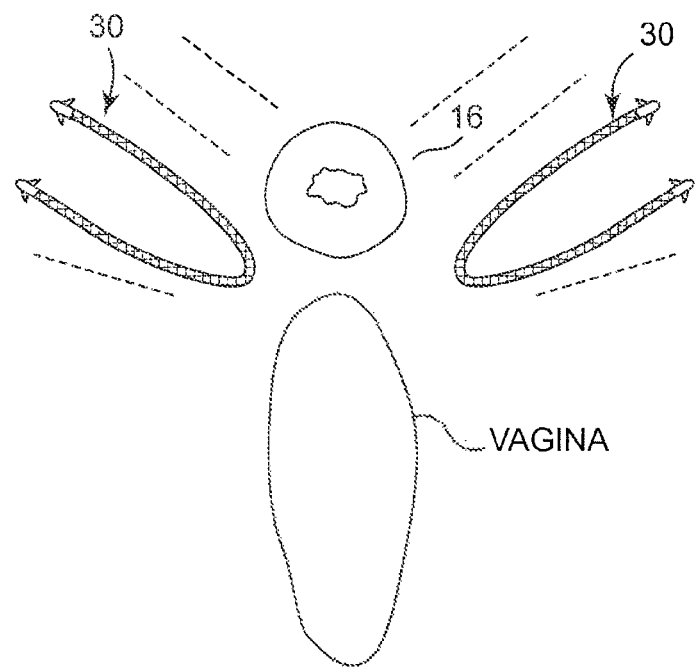
FIG. 18 schematically shows the implantation of U-shaped pelvic implant devices in the lateral urethral support tissue in accordance with embodiments of the present invention.
Figure 19:
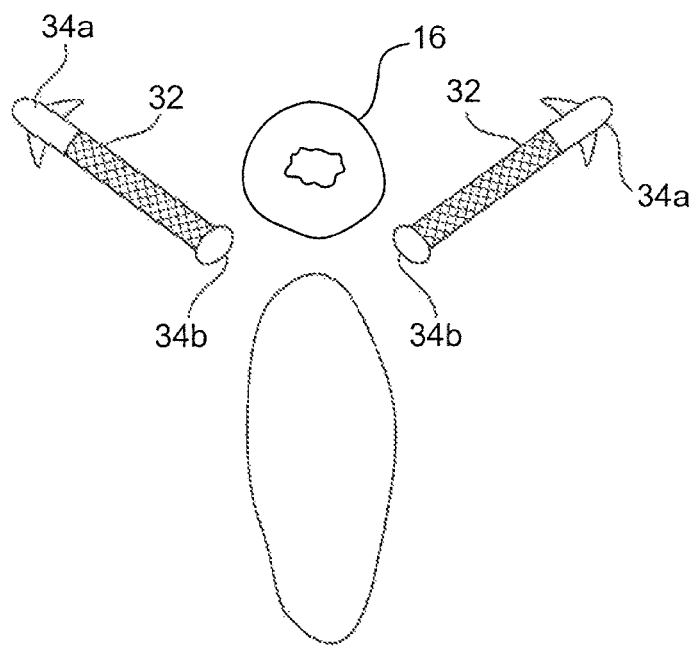
FIG. 19 schematically shows the implantation of implant devices, having leading anchor and trailing bulk anchors, to provide tensioning support for the lateral urethral support tissue in accordance with embodiments of the present invention.

FIG. 18 shows an embodiment of the device 30 having a first anchor 34a and a second anchor 34b, with the portion 32 extending therebetween. The anchors 34a, 34b can be configured in accordance with the various designs disclosed herein. For example, the first anchor 34a can be a penetrating tip, with the second anchor 34a be shaped as a tubular or bulk anchor. One of the anchors can be fixated in tissue above the fascia and the other of the anchors secured at, near or through the fascia to pull the supportive urethral tissue up to eliminate slack in the tissue. This process can be repeated on the other side of the urethra to provide bilateral augmentation and support. Embodiments of the extension portion 32 can be constructed of mesh, or braded, twisted, knitted, tubular, or collagen matrix materials to facilitate fixation and tissue in-growth. Further, a plurality of such devices 30 can be implanted on either or both sides of the urethra to promote tissue augmentation and support.

Figure 20:
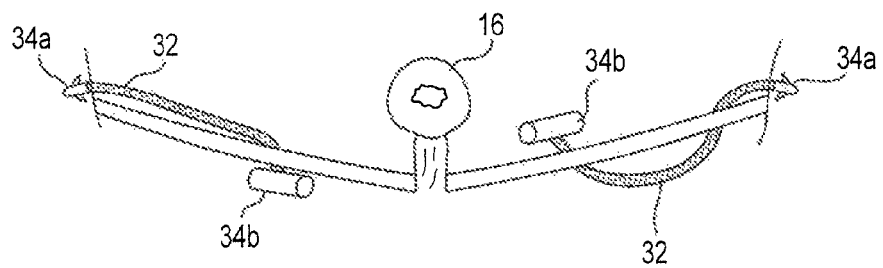
FIGS. 20-21 schematically show the implantation of implant devices, having leading anchor and trailing bulk anchors, to provide tensioning support for the lateral urethral support tissue in accordance with embodiments of the present invention.
Figure 21:
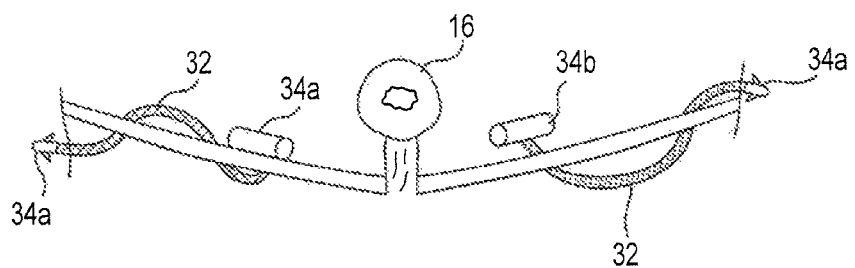

FIGS. 20-21 show certain embodiments of the present invention and devices 30 similar to that depicted in FIG. 16. The bulk anchor 34b (e.g., tubular, toggle (FIG. 26), flat, etc.) can be inserted through the supportive tissue, such as the endopelvic fascia, or it can reside under the supportive tissue, with the anchor 34a extending up through the tissue. As such, either of the anchors 34a, 34b can be positioned on the opposite side of the supportive tissue. Further, at least one of the anchors can serve to penetrate the supportive tissue at one or more locations along the tissue. For instance, certain embodiments of the device 30 can be utilized to weave or thread in and out of, and along, the tissue to provide a supportive undulating layout for the extension portion 32. This can facilitate attachment, better distribute pulling force on or along the tissue, and provide like support benefits.

Figure 22:
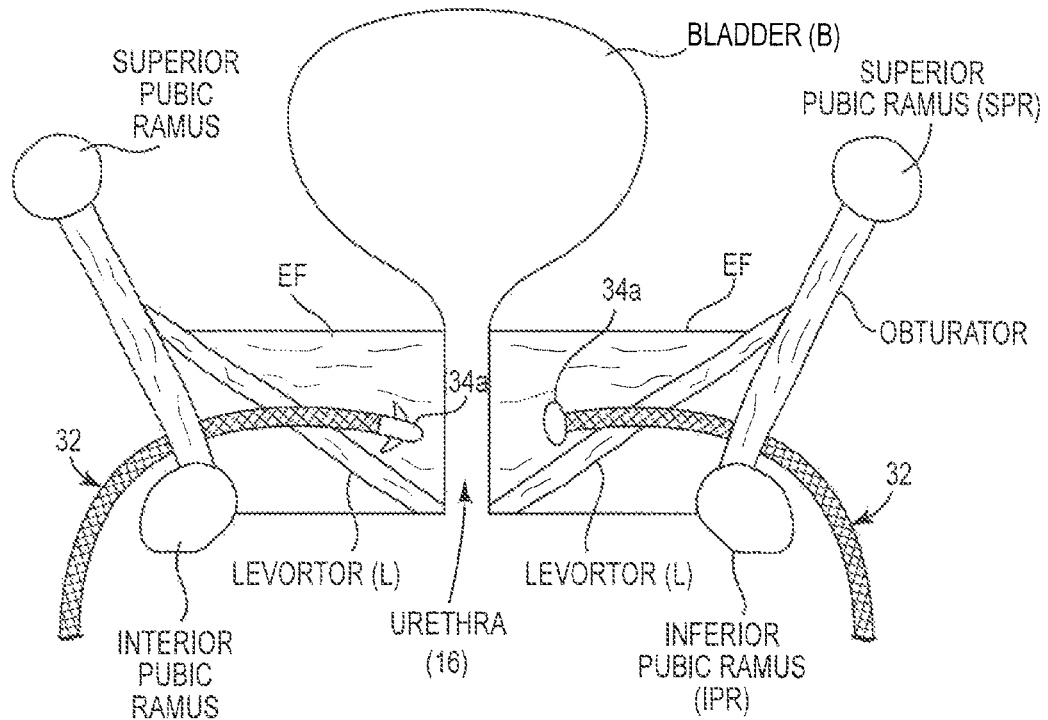
FIGS. 22-23 schematically show the implantation of implant devices through the obturator and into the lateral urethral support tissue in accordance with embodiments of the present invention.
Figure 23:
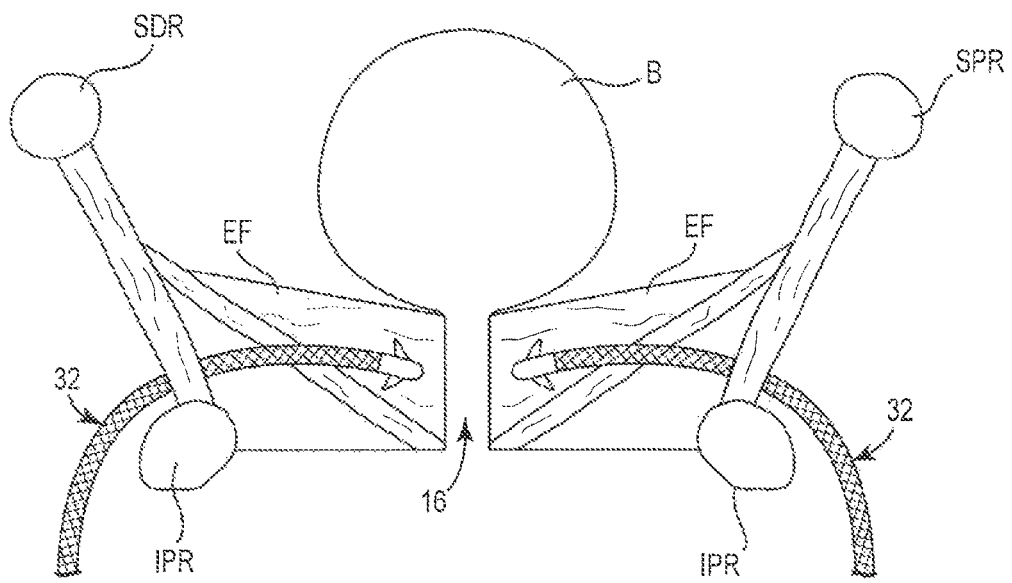

As shown in FIGS. 22-23, an outside-in implant approach can be employed for the device 30. Namely, a skin incision just inferior to where the adductor longus inserts into the pubic ramus can be created. Then, a first anchor 34a of the device 30 can be passed around the ischiopubic ramus and inserted through the obturator foramen and internus muscle and into the tissue lateral to the urethra, e.g., endopelvic fascia that supports the bladder neck and urethra. Once fixated, the device 30 can be pulled to provide tension along the extension portion 32 to augment and return the urethral support tissue to a correct anatomical position. At that point, the proximal opposing end of the device 30 and extension portion 32 can be anchored or otherwise positioned to maintain the tension on the device 30. Any of the needle and/or cannula introducer devices described herein can be employed to insert and deploy the device 30 within the patient. Such an embodiment of the device 30 can provide easier access and patient positioning, can eliminate the need for dissection under the urethra, and can be implanted while the patient is awake such that the device 30 can be selectively adjusted based on indications and movement of the patient. Embodiments of the base or end of the extension portion 32 on the entry side of the tissue could also be glued, sutured or otherwise fixated in or at the tissue using various known structures and techniques. Again, the device 30 can be implanted on either side of the urethra to provide bilateral support. FIG. 23 discloses a variation on this embodiment, with the extension portion 32 being constructed of a non-porous material, such as a suture, polymer material, string, etc.

Figure 24:
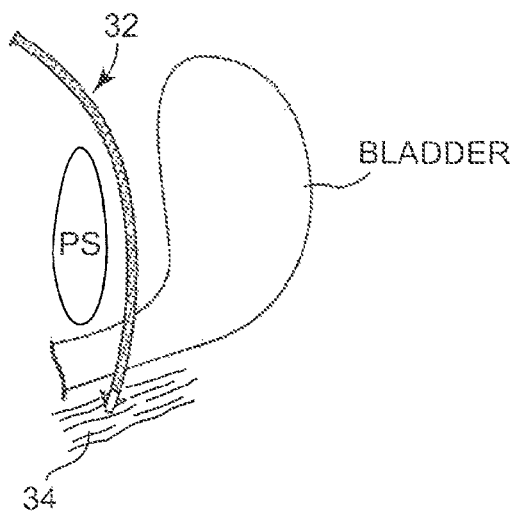
FIGS. 24-25 schematically show the retropubic implantation of implant devices to provide tensioning support for the lateral urethral support tissue in accordance with embodiments of the present invention.
Figure 25:
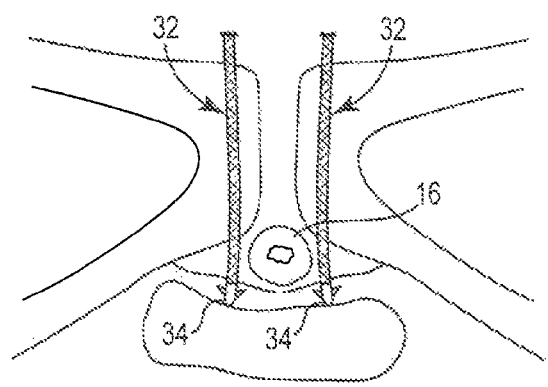
Figure 26:
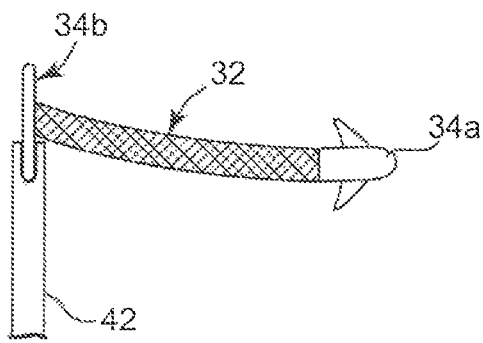
FIG. 26 shows an implant device having a toggle bolt anchor selectively engaged with an introducer device in accordance with embodiments of the present invention.

FIGS. 24-25 depict another embodiment of the implant device 30, introduced along a retropubic path, rather than a transobturator path. One or more skin incisions are generally created such that the device 30 can extend down on either, or both sides of the urethra, with at least one anchor 34 extending into the endopelvic fascia to the anterior vaginal wall. Like the other embodiments disclosed herein, fixation of the implant device 30 to the lateral supporting tissue of the urethra permits adjustment to return the supportive tissue to its correct anatomical position. Again, any of the anchors 34, extension portions 32 and introducer devices described herein can be employed with the embodiment of FIGS. 24-25.

Figure 27:
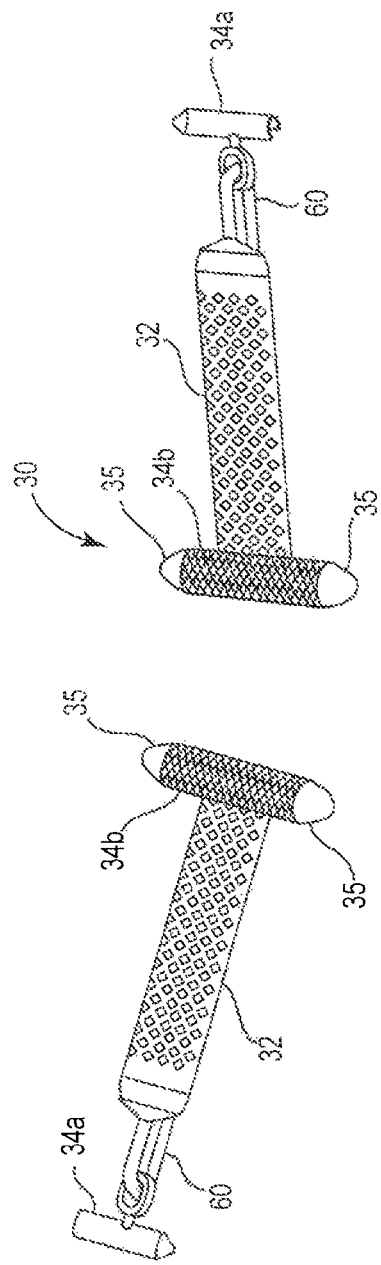
FIG. 27 shows implant devices having a toggle bolt anchor and a tubular base anchor in accordance with embodiments of the present invention.
Figure 28:
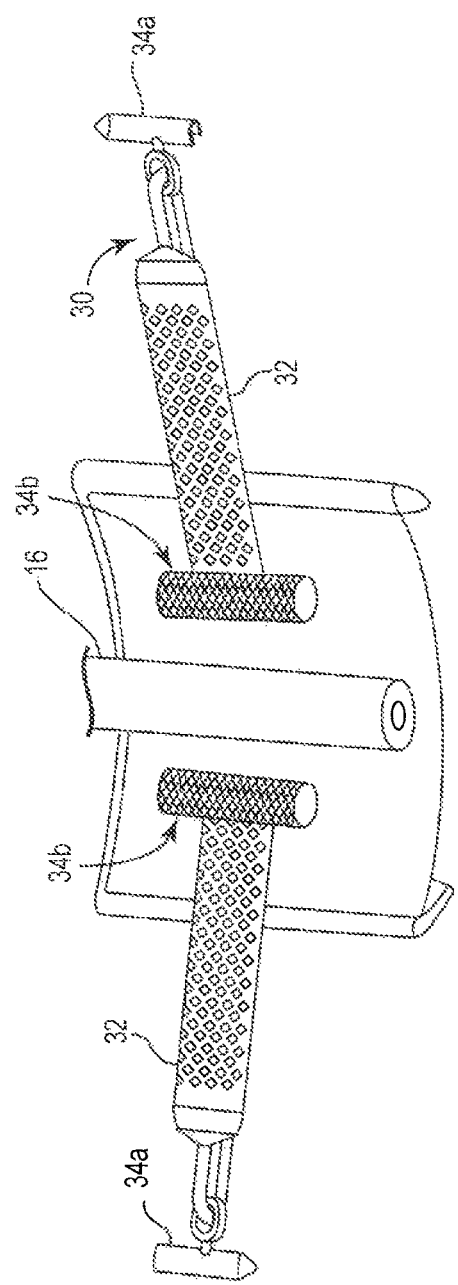
FIG. 28 schematically shows the implantation of the implant devices of FIG. 27 to provide support of the lateral urethral support tissue in accordance with embodiments of the present invention.
Figure 29:
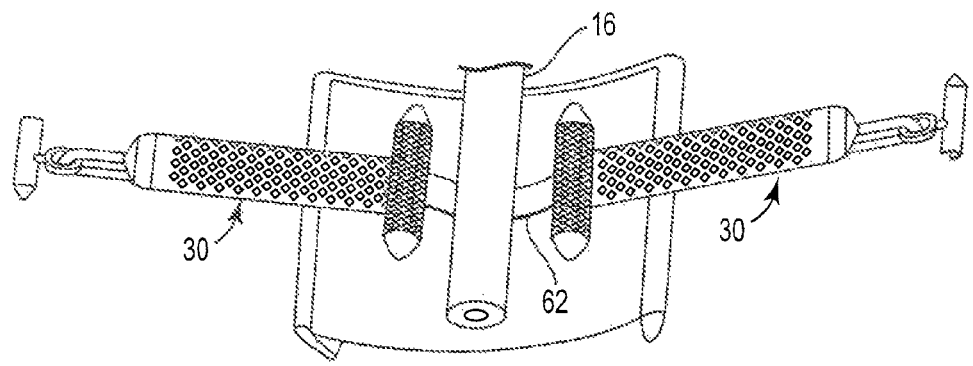
FIG. 29 shows an implant device having a toggle bolt anchor, a tubular base anchor, and an intermediate urethral cradling portion in accordance with embodiments of the present invention.

FIGS. 27-29 show various embodiments of the implant device 30 including engagement or anchoring portions 34a, 34b at each end of the extension portion 32 to provide lateral support of the urethra. The anchors can include any of the structures or features described herein. For example, one embodiment includes a toggle anchor 34a and a tubular (e.g., mesh) base anchor 34b. The tubular base 34b can include cap or other structure 35 provided at its ends. Like other embodiments of device 30, at least one of the anchors, such as tubular base 34b, can be engaged with lateral support tissue of the urethra such that the tissue can be tensioned or raised to remove slack. An adjustment member 60, e.g., rod, suture or like feature, can be included to provide selective adjustment of the device 30 to further facilitate tension control. For those embodiments including tubular engagement features 34b, the features 34b can be of a mesh construction to promote tissue fixation and in-growth. As shown in FIG. 29, this embodiment of the device 30 can further include an intermediate support 62 adapted for positioning under the urethra to provide additional support. The support 62 can be porous or non-porous, and any of the structures (e.g., anchors 34, support 62) can be constructed of re-absorbable or non-absorbable materials.

Figure 31:
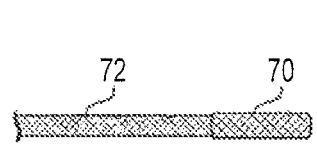
FIG. 31 shows an implant device having a tubular portion and a generally flat portion in accordance with embodiments of the present invention.
Figure 30:
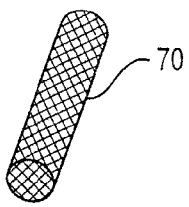
FIG. 30 shows a tubular implant device of device portion in accordance with embodiments of the present invention.
Figure 32:
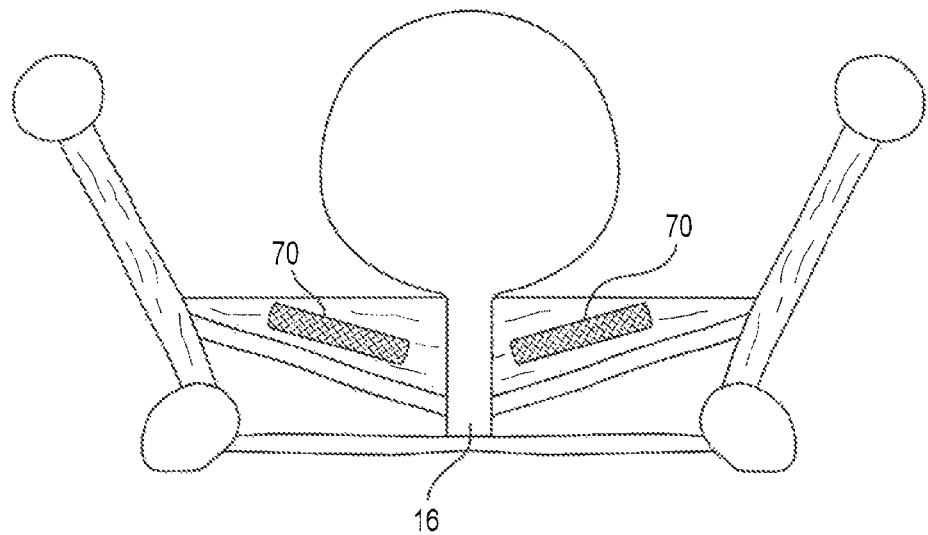
FIG. 32 schematically shows implantation of a tubular and/or flat implant device to provide tensioning support for the lateral urethral support tissue in accordance with embodiments of the present invention.

FIGS. 30-32 depict implants 70 capable of fixation along a portion of the lateral urethral support tissue, e.g., the endopelvic fascia. These implants 70 can include one or more tubular and/or flat mesh structures 72 adapted for engagement with the support tissue to provide adjustment with and/or tension on the tissue. The structures 70, 72 can also be adapted for selective engagement with an introducer device 42 to facilitate insertion and deployment. The implants can be provided without anchors 34, wherein the construct and features (e.g., protrusions, mesh, abrasions, adhesives, fibers, etc.) of the implant can provide the attachment structures necessary to engage with and provide adjustable tension on the support tissue. Other embodiments can include anchors 34 to penetrate or engage the lateral tissue. Further, the implants 70 can be constructed of re-absorbable or non-absorbable materials.

The embodiments of FIGS. 33-38 can include an implant device 80 having a first extension arm 82, a second extension arm 84, and an adjustment member 86 provided with one or both of the extension arms 82, 84. The extension arms 82, 84 can include one or more anchors 88 at their respective ends. The arms 82, 84 can be constructed of a porous mesh, or other materials as described herein for the extension portion 32 of devices 30. Similarly, the anchors 88 can assume the configuration of any of the anchors 34 described herein. Components of the device 80, including the arms and adjustment member, can be constructed of compatible materials such as polypropylene, PGA, PLLA, mesh, braids, ropes, filaments, and the like.

Figures 33, 34:
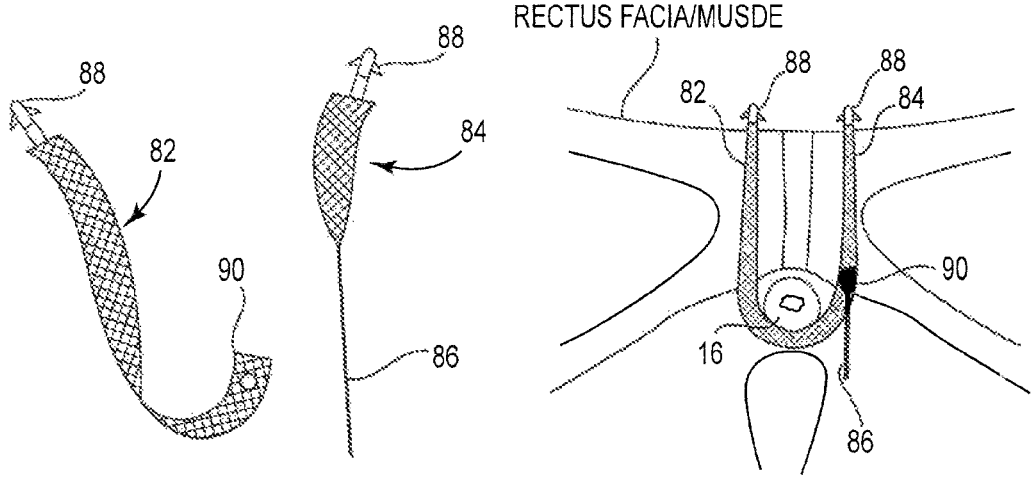
FIG. 33 shows an implant device having a first arm and a second arm in accordance with embodiments of the present invention.
FIG. 34 schematically shows implantation of the implant device of FIG. 33 along a retropubic pathway in accordance with embodiments of the present invention.
Figure 35:
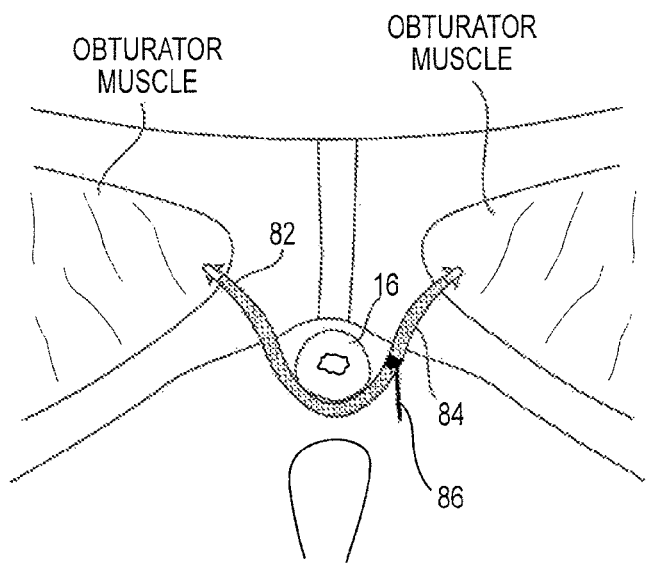
FIG. 35 schematically shows implantation of the implant device of FIG. 33 along a transobturator pathway in accordance with embodiments of the present invention.
Figure 36:
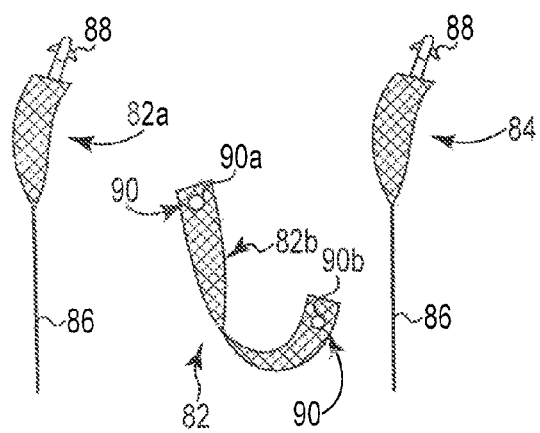
FIG. 36 shows an implant device having a first arm portions and second arm in accordance with embodiments of the present invention.
Figure 37:
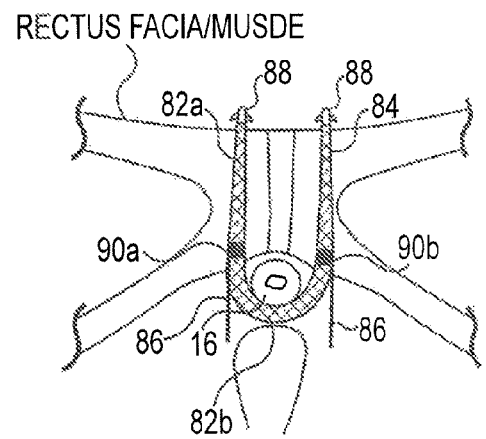
FIG. 37 schematically shows implantation of the implant device of FIG. 36 along a retropubic pathway in accordance with embodiments of the present invention.
Figure 38:
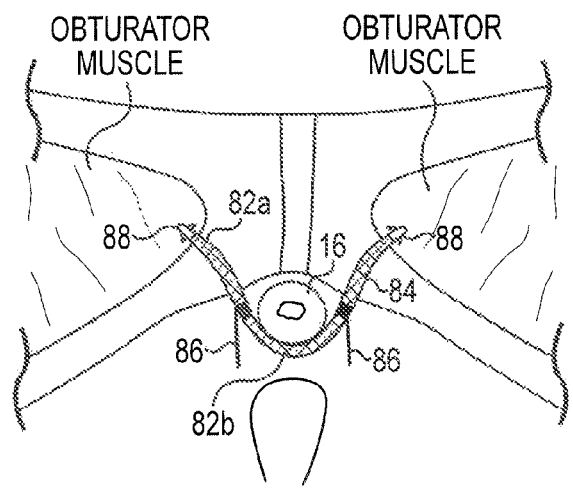
FIG. 38 schematically shows implantation of the implant device of FIG. 36 along a transobturator pathway in accordance with embodiments of the present invention.

Each of the arms 82, 84 (e.g., distinct or separate members) can be passed through one or more vaginal incisions, along a retropubic pathway, until the anchor 88 is secured in tissue, such as the rectus fascia/muscle, as shown in FIGS. 34 and 37. Further, a portion of either arm can extend under the urethra to provide cradling support (e.g., 82 or 82b). To tension the device 80, the member 86 (e.g., rod or polymer extension) of one or both of the arms 82, 84 can be inserted or engaged with an attachment or locking mechanism 90 (e.g., fastener, device, aperture, etc.) of the other arm or implant portion. The member 86 can then be slid along or through the locking mechanism 90 to engage the components until an appropriate tension is obtained. The remaining portion of the member 86 extending below the arms can be cut off and discarded. In other embodiments, each arm 82, 84 could include the member 86, or like adjustment mechanisms, to facilitate balanced or equal tensioning on either side of the urethra. For example, as shown in FIGS. 36-38, the first extension arm 82 includes separate portions 82a and 82b, with the portion 82a adapted for attachment to or through one of the apertures or locking mechanisms 90a of portion 82b, and the other of the apertures or locking mechanisms 90b of portion 82b adapted for receiving the second extension arm 84. As shown in FIGS. 35 and 38, the device 80 can be deployed, and the procedure performed along a transobturator pathway as well, with the anchors 88 being secured in the obturator muscle or like tissue on either side of the pelvis.

For those embodiments having an eyelet or aperture 90 to interconnect the arms 82, 84 or arm portions (e.g., 82a, 82b and 84), various tools (e.g., insertion and push tools), devices, mechanisms (e.g., grommets, and locking or adjustment elements), and techniques can be used to facilitate selective attachment and tensioning of the arms, including those disclosed in U.S. Patent Application Publication No. 2010/0261955, which is hereby incorporated by reference herein in its entirety. Embodiments of the present invention provide key advantages over fixed-length slings, thereby allowing treatment of a large range of patients with a wide range of anatomical dimensions with a single adjustable device.

Figure 39:
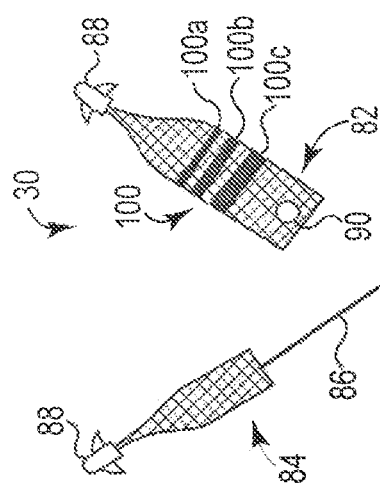
FIG. 39 shows an implant device having arm portions and adjustment indicia in accordance with embodiments of the present invention.
Figure 41:
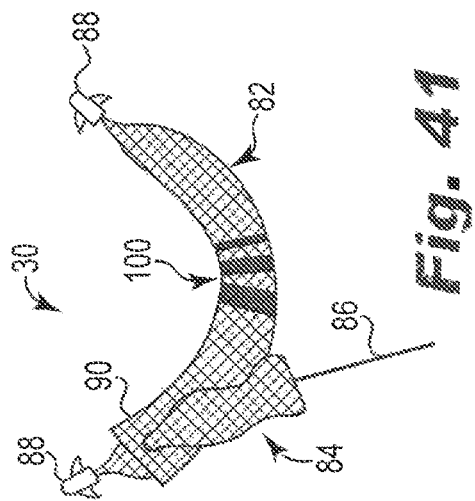
FIGS. 40-41 show slidable adjustment of the implant device of FIG. 39 in accordance with embodiments of the present invention.
Figure 40:
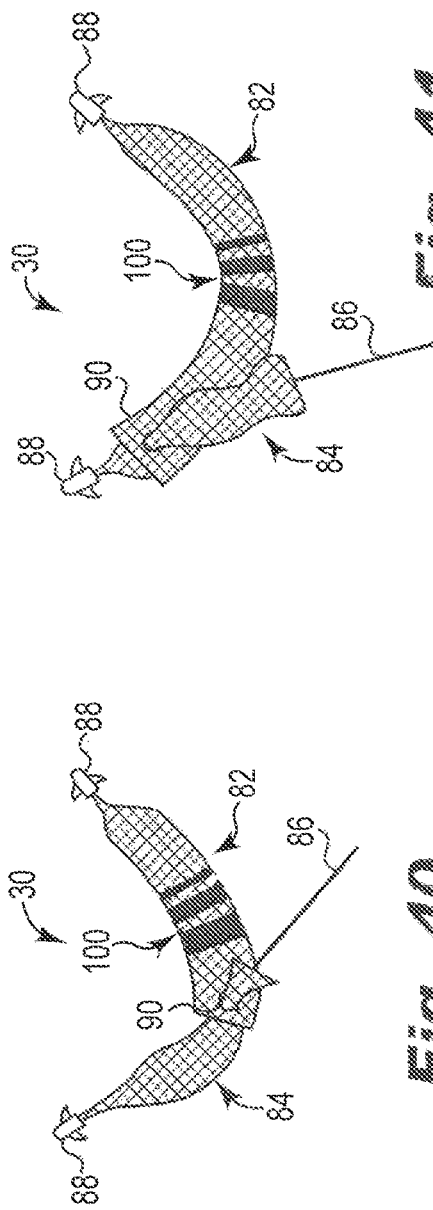

Various sling devices 30, including those having one or more extension arms 82, 84 (e.g., FIGS. 33-38), can include one or more indicia 100 to indicate adjustment, length and positioning thresholds and targets for the physician—e.g., large (100a), medium (100b), small (100c), etc., as shown in FIGS. 39-41. These indicia 100 can be included along any portion of the sling 30, including the portion intended for general central alignment with the anatomical structure to be supported. The indicia 100 can provide broad or granular adjustment indicators, for general alignment, or alignment with anatomical structures such as the urethra, bladder neck, or like structures. The number of indicia 100, and the visual representations, design and look, can vary greatly depending on the particular sling 30 use application. The indicia 100 can be provided to the corresponding portion of the sling 30 with compatible ink, polymer coating, coloring, molding, bonding, or by adding or otherwise including elements that are adapted to stand out (e.g., color, shape, size, design, etc.) along the designated sling portion.

A variety of materials may be used to form portions or components of the implants and devices 30, including Nitinol, polymers, elastomers, porous mesh, thermoplastic elastomers, metals, ceramics, springs, wires, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What we claim is:

1. An elongate implantable incontinence sling system, comprising:
    a tissue support portion having a first eyelet and a second eyelet;
    a first extension arm having a mesh extension, a first anchor portion, and a first rod member, with at least a length of the first extension arm adapted to slide through the first eyelet of the tissue support portion; and
    a second extension arm having a second anchor portion and a second rod member, with at least a length of the second extension arm adapted to slide through the second eyelet of the tissue support portion.

2. The sling system of claim 1, wherein at least a portion of the second extension arm is constructed of a mesh material.

3. The sling system of claim 1, wherein at least one of the first and second rod members is a polymer extension rod.

4. The sling system of claim 1, wherein the first and second rod members are polymer extension rods.

5. The sling system of claim 1, further including a grommet adapted to engage at least one of the first and second eyelets to facilitate attachment of the first extension arm or the second extension arm.

6. The sling system of claim 1, further including one or more alignment indicia provided along a portion of the tissue support portion.

7. The sling system of claim 6, wherein the one or more indicia includes three indicia adapted to guide placement of the elongate sling relative to tissue targeted for support.

8. The sling system of claim 1, wherein the anchor portion of at least one of the first and second extension arms is adapted to engage with obturator tissue.

9. The sling system of claim 1, wherein the anchor portion of at least one of the first and second extension arms is adapted to engage with rectus fascia.

10. The sling system of claim 1, wherein the tissue support portion spans under and provides support to the urethra.

11. An elongate implantable incontinence sling system, comprising:
    a tissue support portion having a first eyelet and a second eyelet;
    a first extension arm having a first anchor portion, an elongate first mesh portion, and a first rod member, with at least a length of the first elongate mesh portion adapted to slide through the first eyelet of the tissue support portion; and
    a second extension arm having a second anchor portion, a second elongate mesh portion, and a second rod member, with at least a length of the second elongate mesh portion adapted to slide through the second eyelet of the tissue support portion, such that the tissue support portion spans under and provides support to the urethra.

12. The sling system of claim 11, further including a grommet adapted to engage at least one of the first and second eyelets to facilitate attachment of the first extension arm or the second extension arm.

13. The sling system of claim 11, further including one or more alignment indicia provided along a portion of the tissue support portion.

* * * * *